United States Patent [19]

Fogarty et al.

[11] Patent Number: 4,564,014
[45] Date of Patent: Jan. 14, 1986

[54] VARIABLE LENGTH DILATATION CATHETER APPARATUS AND METHOD

[75] Inventors: Thomas J. Fogarty, 770 Welch Rd., Palo Alto, Calif. 94304; Albert K. Chin, San Francisco, Calif.

[73] Assignee: Thomas J. Fogarty, Palo Alto, Calif.

[21] Appl. No.: 116,923

[22] Filed: Jan. 30, 1980

[51] Int. Cl.⁴ ............................................. A61M 29/02
[52] U.S. Cl. .................................. 128/344; 128/348.1
[58] Field of Search ............ 128/344, 349 B, 349 BV, 128/325, 304

[56] References Cited

U.S. PATENT DOCUMENTS

| | | | |
|---|---|---|---|
| 3,433,215 | 3/1969 | Silverman | 128/768 |
| 3,833,003 | 9/1974 | Taricco | 128/347 |
| 3,834,394 | 9/1974 | Hunter et al. | 128/325 |
| 3,896,815 | 7/1975 | Fettel et al. | 128/348 |
| 3,978,863 | 9/1976 | Fettel et al. | 128/348 |
| 3,996,938 | 12/1976 | Clark | 128/348 |
| 4,195,637 | 4/1980 | Gruntzig et al. | 128/348 |

Primary Examiner—Michael H. Thaler
Attorney, Agent, or Firm—Limbach, Limbach & Sutton

[57] ABSTRACT

A dilatation catheter comprising an elongate elastomeric tube having a telescopic sheath received therearound to selectively expose varying lengths of tube or inflation. A wire extending through the tube provides for longitudinal stretching of the tube to reduce it diametrical cross-section. In one embodiment, port means within the tube may be exposed by contracting of the sheath to provide means whereby injections may be made through the tube.

16 Claims, 7 Drawing Figures

VARIABLE LENGTH DILATATION CATHETER APPARATUS AND METHOD

BACKGROUND OF THE INVENTION

The present invention relates to a method and apparatus for use in dilating occluded blood vessels. The invention is particularly concerned with such a method and apparatus wherein dilatation is achieved through means of a balloon element which is inflated to compress the occlusion being treated and wherein the length of the element may be selectively adjusted to vary the length of the occlusion subject to compression. The invention is intended for use in treating either arterial or venous occlusions.

RELATED APPLICATION

The present application is related to copending application Ser. No. 114,982, filed Jan. 24, 1980, by Thomas J. Fogarty, one of the applicants herein. That application is also concerned with a method and apparatus for compressing an occlusion within a blood vessel for purposes of increasing the patency of the vessel. It differs materially from the present application in that the inflatable balloon disclosed therein is not provided with an adjustable sheath to selectively vary the inflatable length of the balloon.

SUMMARY OF THE INVENTION

In the method and apparatus of the present invention, an elongated elastomeric tube is confined within a sheath which may be selectively retracted to increase the length of the tube exposed for inflation. Retraction may be achieved while the tube is within a vessel being treated. Thus, during the course of treatment, the length of the occlusion subjected to dilatation by inflation of the balloon may be progressively increased. The tube is deflated during retraction of the sheath and in the course of placement of the tube within the vessel being treated. A wire is provided to selectively elongate the tube and reduce its diametrical cross-section.

A principal object of the invention is to provide a method of dilating an occluded blood vessel by subjecting the vessel to expansive compression and progressively increasing the length of the occlusion subjected to such compression.

Another object of the invention is to provide an inflatable dilatation catheter wherein the length of the inflatable element may be selectively varied while the element is within a vessel being treated.

Still another object of the invention is to provide such a catheter wherein adjustment of the length of the inflatable element is provided by confining the element within a retractable sheath.

Yet another object of the invention is to provide such a catheter wherein a guide wire is provided within the inflatable element to selectively stretch the element and decrease its uninflated diametrical cross-section for purposes of facilitating placement of the catheter and movement of the sheath.

Yet another and more general object of the invention is to provide a catheter whereby an extended length of arterial occlusion may be incrementally and progressively dilated.

A further object of the invention is to provide such a catheter wherein the inflatable element is provided with a port which may be selectively exposed by retraction of the sheath to permit injections to be made through the port.

The foregoing and other objects will be more apparent when viewed in light of the following description and accompanying drawings.

DETAILED DESCRIPTION

Figure 1:
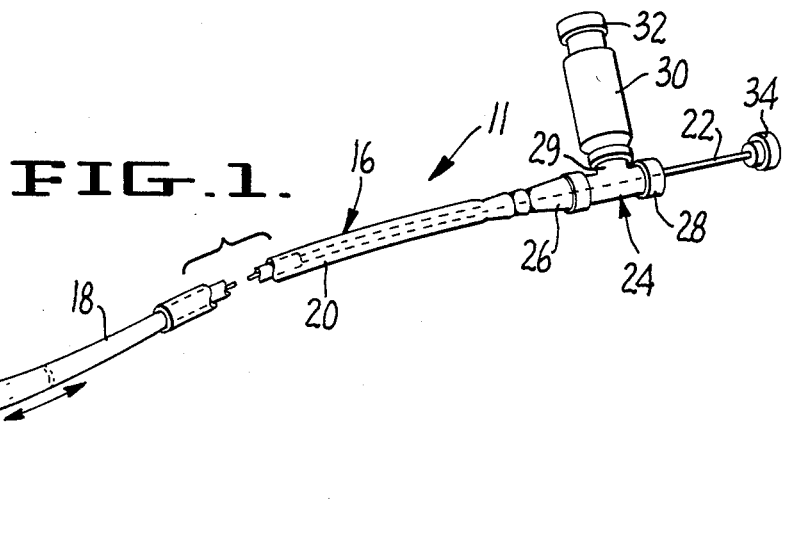
FIG. 1 is a perspective view illustrating an occluded vessel in the process of having the catheter of the present invention placed therein.

FIG. 1 illustrates a blood vessel 10, partially occluded by an extended occlusion 12. As shown, the vessel takes the form of an artery and the occlusion is what is commonly known as an arteriosclerotic plaque or atheroma. This is the type of adhering occlusion with which the inventive apparatus and method is expected to find primary application. It should be understood, however, that the invention is applicable in treating other types of occluded vessels where dilatation is desired. For example, the invention may be used in treating occlusions resulting from fibromuscular displasia in veins.

The catheter, designated 11, comprises: an elongate elastomeric tube 14 closed at its distal end and extending the full length of the catheter; a telescopic sheath 16 received around the tube 14 and having a distal primary section 18 movable relative to the tube and a proximal secondary section 20 secured against movement relative to the tube; and a guide wire 22 disposed within and extending through the full length of the tube 14, said wire having the distal end thereof secured to the distal end of the tube and the proximal end thereof extending from the proximal end of the tube. A T-shaped coupling 24 is sealingly secured to the proximal end of the tube 14 by a tapered snout 26. The coupling provides an axially extending branch 28 through which the wire 22 extends, and a laterally extending branch 29 to which a syringe 30 is secured. The syringe 30 is engaged in sealed fluid communication with the branch 28 and has a piston 32 for displacing fluid. A knob 34 is secured to the proximal end of the wire 22 externally of the coupling 24. Packing within the branch 28 slidably and sealingly engages the wire 22 to prevent the escape of fluid therearound.

Figure 5:
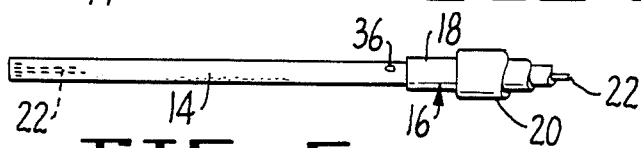
FIG. 5 is an elevational view of the catheter, with parts thereof broken away, illustrating a port within the inflatable element and the sheath retracted to a position to expose the port.
Figure 6:
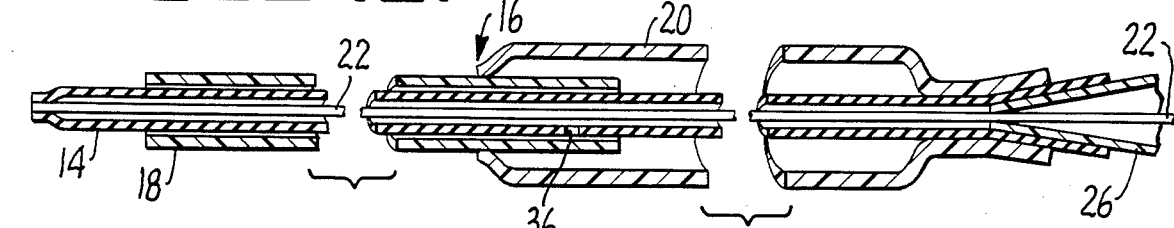
FIG. 6 is an enlarged cross-sectional elevational view of the catheter.
Figure 7:
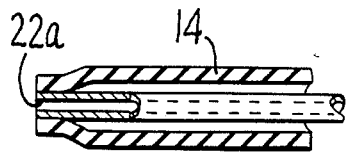
FIG. 7 is an enlarged cross-sectional elevational view of the catheter, showing the distal end only of an alternative embodiment wherein the wire extending through the inflatable element is of tubular configuration.

The tube 14 may be fabricated of any suitable elastomeric material, such as silicon or rubber. "Silastic" tubing by DuPont has been found to be suitable. In the embodiment shown in FIGS. 5 and 6, a port 36 is formed within the body of the tube at an intermediate portion thereof normally covered by the primary section 18 of the telescopic sheath. This port is provided so that a contrast fluid may be injected therethrough into the vessel being treated. When the section 18 is over the port, the port is closed. Thus, the section 18 provides means whereby the port may be selectively opened or closed. As an alternative to providing the port 36 for injection purposes, the wire extending through the catheter may take the form of a hollow flexible tube 22a, as shown in FIG. 7. The tube 22a extends through the distal end of the tube 14 and is open to provide for the injection of fluid therethrough.

The primary section 18 is fabricated of a highly flexible generally inelastic material, such as Dacron, and proportioned to snugly and slidably receive the tube 14 when the tube is in an uninflated condition. To facilitate slidable movement of the section 18 relative to the tube 14, the tube may be stretched lengthwise, and thus reduced in diametrical cross-section, by extending the wire 22. Such extension may also prove useful when inserting the catheter into a constricted section of a vessel being treated.

The section 20 is also fabricated of a relatively inelastic flexible material. The distal end of the section 20 is of a reduced internal diameter to telescopically and sealingly engage the outside surface of the section 18. The proximal end of the section 20 is snugly received around the end of the tube 14 within which the snout 26 is engaged. As a result of the latter characteristic, the section 20 serves to assist in securing the tube 18 to the snout 26. Although the section 20 is shown as having an enlarged intermediate portion between the distal and proximal ends thereof, it should be understood that this intermediate portion could be of an internal diameter closely approximating the external diameter of the section 18. Such a reduced internal diameter would actually be advantageous, since it would further restrict against inflation that portion of the tube 14 exposed to the interior of the section 20.

In use, the catheter is inserted into the vessel being treated through an incision made for that purpose. Once within the vessel, the catheter is fed therethrough, as depicted in FIG. 1, to the situs to be treated. During the course of such feeding, the tube 14 and the distal portion of the section 18 are directed into the vessel, while the proximal portion of the section 18 is maintained externally of the vessel within the control of the physician. Thus, the physician maintains full control of the catheter and the position of the section 18 relative to the tube 14.

Figure 2:
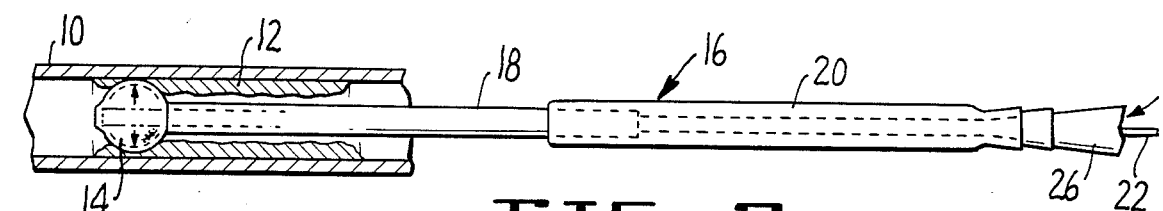
FIG. 2 is an elevational cross-sectional view illustrating the catheter within the vessel with the distal end only of the catheter inflated and the sheath positioned to constrain all but the distal end against inflation.
Figure 3:
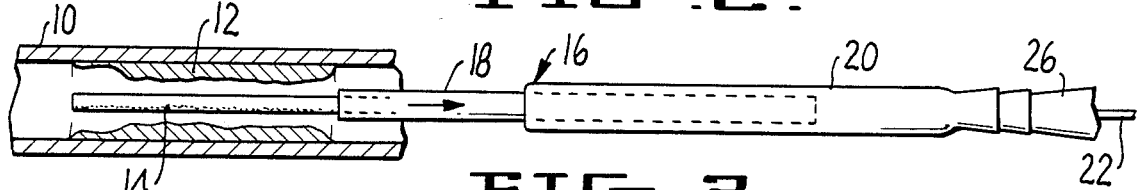
FIG. 3 is an elevational cross-sectional view, illustrating the catheter in an uninflated condition and disposed within the vessel, with the sheath in the process of being retracted from the inflatable element of the catheter.

Once the catheter is within the occlusion to be treated, the position of the catheter and the sheath section 18 are adjusted, as seen in FIG. 2, and the tube is subjected to internal fluid pressure by compressing the piston 32. Such pressure functions to expand the distal end of the tube 14 and compress the limited section of the occlusion disposed therearound. Thereafter, the tube 14 is deflated and stretched through extension of the wire 22 and the sheath section 18 is retracted to expose an extended length of the tube, as shown in FIG. 3. The wire 22 is then relaxed and the tube 14 is once again subjected to internal pressure through compression of the piston 32, thus expanding the entire length of the exposed tube into compressing relationship with the occlusion, as shown in FIG. 4.

Figure 4:
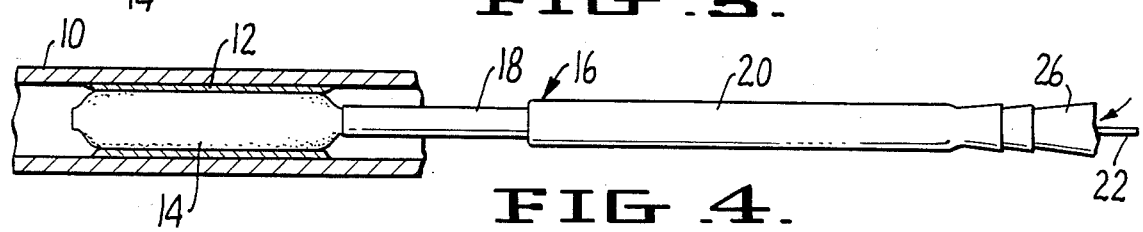
FIG. 4 is a cross-sectional elevational view, similar to FIG. 3, illustrating the inflatable element after it has been inflated to dilate an extended length of the occlusion being treated.

Although the sequence shown in FIGS. 2, 3 and 4 of the drawings illustrates but a single increment of withdrawal of the sheath section 18, it should be understood that the sheath section may be gradually withdrawn through means of a plurality of successive increments, with the tube being inflated after each increment of withdrawal to progressively compress increasingly larger lengths of the occlusion being treated. It should also be understood that after treatment of an isolated occlusion within a vessel, the catheter may be directed to other occlusions within the vessel and reapplied to treat these occlusions so as to increase their patency.

During the course of positioning the catheter, a contrast medium, such a radio opaque fluid, may be injected into the vessel being treated through the port 36. Such injection would be carried out with the tube 14 in an uninflated condition and the sheath section 18 retracted to expose the port 36.

CONCLUSION

The apparatus and method of the present invention are ideally suited for the dilatation of elongate arterial occlusions through the achievement of precise progressive and incremental dilatation. It should be understood, however, that the invention is not intended to be limited to the specifics of the embodiments herein illustrated and described, but rather is defined by the accompanying claims.

What is claimed is:

1. A catheter for dilating a partially occluded blood vessel, said catheter comprising: an elongate inflatable elastomeric tube extending substantially the full length of the catheter and proportioned for extension through the vessel; means to inflate the tube; a primary non-inflatable sheath telescopically positioned around the tube in closely fitting relationship thereto confining a predetermined portion of the inflatable length of the tube against inflation, said sheath being proportioned for extension through the vessel with the tube and being longitudinally movable relative to the tube to selectively expose varying distal portion lengths of the tube for inflation.

2. A catheter according to claim 1, further comprising a guide wire disposed within the tube and connected to the distal end thereof, said wire being longitudinally extensible relative to the tube to selectively impart a variable stretching force to the tube.

3. A catheter according to claim 1, further comprising a secondary sheath telescopically and slidably fitted about the primary sheath, said primary sheath being longitudinally movable into and out of the secondary sheath whereby the cumulative length of the primary and secondary sheaths may be selectively varied to vary the distal length portion of the tube to be inflated.

4. A catheter according to claim 3, wherein: the means to inflate the tube comprises a syringe having a tapered coupling extending into the proximal end of the tube; and the secondary sheath snugly embraces the proximal end of the tube to secure the coupling therein.

5. A catheter according to claim 2, further comprising a coupling secured in fluid communication with the tube, said coupling having: a branch extending laterally from the tube for connection thereto of the means to inflate the tube; and a branch extending longitudinally of the tube, said branch having packing therein through which the guide wire sealingly and slidably extends.

6. A catheter according to claim 1 wherein: the tube has a port extending therethrough; and, the primary sheath is movable relative to the tube to selectively open and close said port.

7. A catheter for dilating a partially occluded blood vessel, said catheter comprising: an elongated inflatable elastomeric tube extending substantially the full length of the catheter and proportioned for extension through the vessel, said tube having a sealed distal end and an open proximal end; means connected in sealed fluid communication with the proximal end of the tube to inflate the tube by imparting internal fluid pressure thereto; a primary non-inflatable sheath telescopically positioned around said tube in closely fitting relationship thereto confining a predetermined portion of the inflatable length of the tube against inflation, said sheath being porportioned for extension through the vessel with the tube and being longitudinally movable relative to the tube to selectively expose varying distal portion lengths of the tube for inflation; and a guide wire extending through the tube, said wire having one end secured to the distal end of the tube and the other end extending from the proximal end of the tube whereby the wire may be extended relative to the tube to variably stretch the tube and reduce its diametral cross-section to facilitate movement of the sheath relative to the tube and placement of the tube within confined sections of a vessel being treated.

8. A catheter according to claim 7, further comprising a secondary sheath telescopically and slidably fitted about the primary sheath, said primary sheath being longitudinally movable into and out of the secondary sheath whereby the cumulative length of the primary and secondary sheaths may be selectively varied to vary the distal length portion of the tube to be inflated.

9. A catheter according to claim 8 wherein: the means to inflate the tube comprises a syringe having a tapered coupling extending into the proximal end of the tube; and the secondary sheath snugly embraces said proximal end of the tube to secure the coupling therein.

10. A catheter according to claim 7, further comprising a coupling secured in sealed fluid communication with the proximal end of the tube, said coupling having: a branch extending laterally from the tube for connection thereto of the means to inflate the tube; and, a branch extending longitudinally of the tube, said branch having packing therein through which the guide wire sealingly and slidably extends.

11. A catheter according to claim 2 or 7, wherein the wire is provided with an axial passageway communicating with the atmosphere through the distal end of said tube.

12. A method of dilating a partially occluded blood vessel, said method comprising: confining at least part of the length of an elongated elastomeric tube within a sheath to restrict the length of the tube so confined against inflation; inserting the tube, with the sheath therearound, into the vessel; directing the tube to the situs of the vessel to be treated; positioning the sheath to expose the distal end of the tube for inflation; successively inflating and deflating the exposed end of the tube to move the tube into and out of compressing engagement with the vessel; and incrementally withdrawing the sheath from the tube to progressively increase the length of the tube exposed for inflation.

13. A method according to claim 12 wherein the tube is deflated and longitudinally stretched to reduce its diametrical cross-section during the process of directing the tube to the situs of the vessel to be treated.

14. A method according to claim 12, wherein the tube is deflated and longitudinally stretched to reduce its diametrical cross-section during incremental withdrawal of the sheath.

15. A method according to claim 12, further comprising providing at least one port in the length of the tube confined by the sheath and selectively withdrawing the sheath from the tube to expose the port whereby injections may be made therethrough.

16. A method according to claim 12, wherein the sheath confining the tube is telescopic and withdrawal of the sheath from the tube is achieved by telescopically foreshortening the tube to reduce its composite length.

* * * * *